United States Patent [19]

Van Gompel et al.

[11] Patent Number: 4,677,695
[45] Date of Patent: Jul. 7, 1987

[54] WEB WITH ADJUSTABLE OPENING AND METHOD OF MAKING THE SAME

[75] Inventors: Paul T. Van Gompel, Outagamie County; Jody D. Suprise, Winnebago County, both of Wis.

[73] Assignee: Kimberly-Clark Corporation, Neenah, Wis.

[21] Appl. No.: 827,297

[22] Filed: Feb. 6, 1986

[51] Int. Cl.$^4$ ............................ A41D 1/06; B32B 3/10
[52] U.S. Cl. ............................................. 2/79; 2/237; 2/227; 428/137; 428/172; 428/212
[58] Field of Search ..................... 428/137, 212, 172; 2/79, 237, 227

[56] References Cited

FOREIGN PATENT DOCUMENTS 394528 6/1933 United Kingdom ............... 428/137

Primary Examiner—Alexander S. Thomas
Attorney, Agent, or Firm—Douglas L. Miller; Donald L. Traut; Jeremiah J. Duggan

[57] ABSTRACT

A composite with an adjustable, conformable opening therein, comprising a base web of less extensible, lower elastic recovery material, joined to a second web, of more extensible, higher elastic recovery material, wherein the base web has a first opening therein, and the second web has a second opening therein generally concentric with the first opening and of smaller size than the first opening, so that the second opening is circumferentially peripherally bounded by an annular-shaped segment of the second web, and the annular-shaped segment of the second web in turn is circumferentially peripherally bounded by the base web. The composite is advantageously employed to form garments and similar articles wherein the opening serves as a conformable, adjustable body part opening, such as in gloves, shirts, socks, shoe covers, slippers, disposable diapers, training pants, etc.

13 Claims, 9 Drawing Figures

WEB WITH ADJUSTABLE OPENING AND METHOD OF MAKING THE SAME

BACKGROUND OF THE INVENTION

1. Field of the Invention

This invention generally relates to webs with adjustable openings and to a method of making the same, and more specifically to a garment with a conformable body part opening and to a method of making the same.

2. Description of the Related Art

U.S. Pat. No. 4,446,189 to G. A. Romanek discloses a nonwoven textile fabric laminate comprising an inner layer of generally elastic material of inherent resilience, on at least one side of which is superposed an outer layer comprising a generally inelastic nonwoven textile fabric comprising a plurality of generally coherent nonwoven fibers. The nonwoven textile fabric is extensible from a relaxed position to a point beyond its elastic limit and is incapable of self-induced retraction to its original relaxed condition upon release of the tensioning force. The respective elastic and nonwoven layers are needle-punchingly secured together at spaced-apart locations by nonwoven fibers of the fabric which extend through the inner elastic layer at the securement locations when the inner and outer layers are stretched with the elastic layer within its elastic limit and the nonwoven layer beyond its elastic limit. The first outer layer thus exhibits increased bulk between the securement locations when the inner layer retracts to its relaxed condition.

U.S. Pat. No. 3,912,565 to W. T. Koch, et al. describes a method of preparing a shirred, elastic, flexible article by attaching to a sheet material a thin layer of flexible polyurethane material which is heat-shrinkable in only one direction, followed by heating the polyurethane layer to shrink and shirr the sheet material attached thereto.

U.S. Pat. No. 3,331,728 discloses a perforate film-fiber laminate for the use of wound dressings and the like. The laminate is prepared of thin flexible film adhered to a pervious substrate, with the film having openings therein immediately overlying openings in the substrate. A fiber substrate, including woven and nonwoven fabrics, containing pre-formed openings passing directly therethrough may advantageously be coated with a freshly extruded thermoplastic film, e.g., polyethylene, which is simultaneously perforated and adhered to the surface by drawing a sufficiently high vacuum on the surface opposite to that to which the film has been applied, sufficient to burst the film, while still highly plastic, in areas immediately over the openings in the fiber substrate.

European Patent Application No. 102,245 of I. S. Ness discloses an extensible elastic composite with elastic recovery formed by intermittently securing an elastic member to a substrate which prior to initial stretching is less easily extensible than the elastic member. More specifically, this reference discloses an elastic composite for disposable diapers, comprising a reticulated elastic layer bonded between EVA coated less extensible plastic films.

SUMMARY OF THE INVENTION

In one aspect, the present invention relates to a composite with an adjustable, conformable opening therein, comprising a base web of less extensible, lower elastic recovery material, joined to a second web, of more extensible, higher elastic recovery material, wherein the base web has a first opening therein, and the second web has a second opening therein generally concentric with the first opening and of smaller size than the first opening, so that the second opening is circumferentially peripherally bounded by an annular-shaped segment of the second web, and the annular-shaped segment of the second web in turn is circumferentially peripherally bounded by the base web.

In another aspect, the present invention relates to a method of making a composite web with an adjustable opening, comprising the steps of providing a base web of less extensible, lower elastic recovery material, cutting a first opening therein, joining to the base web a second web of more extensible, higher elastic recovery material so that said second web overlays said first opening in the base web, cutting a second opening in the second web which is generally concentric with the first opening and of smaller size than the first opening, so that the second opening is circumferentially peripherally bounded by an annular-shaped segment of the second web, and the annular-shaped segment of the second web in turn is circumferentially peripherally bounded by the base web.

In another aspect, the present invention relates to a garment with a conformable body part opening, comprising the aforementioned composite web.

Another aspect of the present invention relates to a composite web, comprising a second web having a second opening therein as previously described, and contiguously joined on either side thereof to a base web having a first opening therein as previously described, to form a multilayer composite wherein the second web is interposed between base web outer layers.

In another aspect, the base web is a fibrous substrate, which may be woven or nonwoven in character, and the second web is a thermoplastic and/or elastomeric film which is joined to the base web by lamination or melt extrusion of the film onto the base web.

Yet another aspect of the invention relates to a pant-type garment with conformable leg openings, formed of superposed front and back panels joined to one another along side and central bottom portions, with the respective side and central bottom portions separated from each other by unjoined arcuately contoured portions of the front and rear panels to form leg openings from the garment, wherein the front and rear panels of the garment at least in the vicinity of the leg openings are formed of a composite comprising a base web of less extensible, lower elastic recover material joined to a second web, of more extensible, higher elastic recovery material, wherein the leg openings are circumferentially bounded by annular arcuate segments of only said second web, extending from said composite comprising said base web and second web.

Still another aspect of the present invention relates to a method of making a pant-type garment of such type, comprising the steps of providing a longtudinally extending base web of less extensible, lower elastic recovery material, cutting first openings at longitudinally spaced-apart intervals in a central longitudinal portion of the base web, joining the base web to a second web of more extensible, higher elastic recovery material to form a composite web therefrom, in which the second web overlays the first openings in the base web, cutting second openings in the second web which are generally concentric with the first openings and of smaller size than the first openings, so that the second openings are circumferentially peripherally bounded by annular-shaped segments of the second web and the annular-shaped segments of the second web in turn are circumferentially peripherally bounded by the base web, longitudinally folding the composite web along a line intersecting the first and second openings, bonding the folded composite web along longitudinally spaced-apart, transversely extending bands intersecting the first and second openings, and medially severing the transversely extending bands, to form discrete severed articles as said pant-type garments.

Other aspects and features of the present invention will be apparent from the ensuing disclosure and appended claims.

DETAILED DESCRIPTION OF THE PREFERRED EMBODIMENTS

Figure 1:
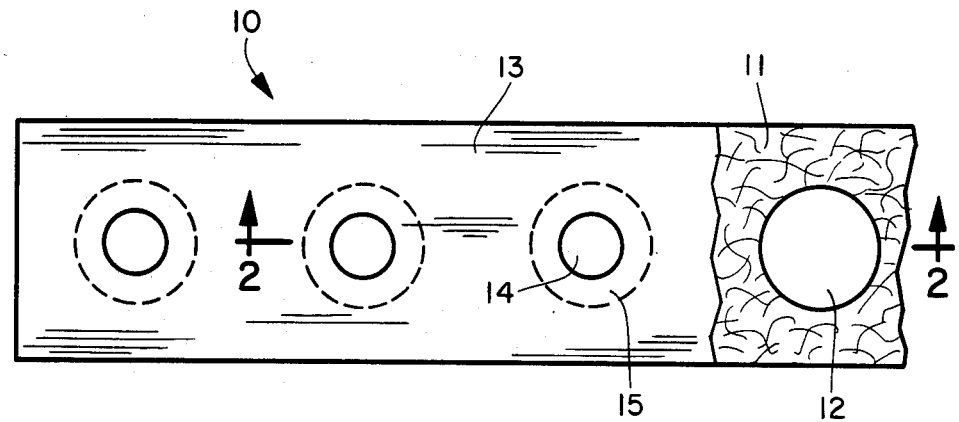
FIG. 1 is a partial sectional plan view of a composite web according to one embodiment of the present invention.

In the composite according to the present invention, featuring an adjustable conformable opening therein, a first layer of less extensible, lower elastic recovery material is provided as a base web serving as a substrate for a layer of more extensible, higher elastic recovery material as a second web of the composite.

The base web in such construction has a first opening therein which is of larger size than a second opening in the second web generally concentric therewith, so that the second opening is circumferentially peripherally bounded by an annular-shaped segment of the second web, the annular-shaped segment in turn being circumferentially peripherally bounded by the base web surrounding and defining the first opening.

In other words, the second web overlays the base web with generally concentrically aligned openings, the base web opening being larger in size than the second web opening so that only the second web material extends circumferentially and inwardly from the base web opening toward the second opening. In such manner, a "ring" of the second web material is provided at the opening, which being more extensible and characterized by higher elastic recovery than the base web material provides a stretchable resilient opening in the composite.

The composite thus is advantageously employed to form garments and similar articles wherein the opening serves as a conformable, adjustable body part opening, such as in gloves, shirts, socks, shoe covers, slippers, disposable diapers, training pants, etc. In such case, the second web material, being more extensible and possessed of higher elastic recovery than the first material, provides yielding adjustment to inserted body parts of larger size than the second opening therein, such that the opening stretches to the appropriate size and due to its higher elastic recovery (relative to the base web material), maintains circumferentially effective tension for conformable fit of the garment.

The base web material in turn circumferentially surrounding the "ring" of second web material provides reinforcement for the opening and, since the base web material is less extensible and has lower elastic recovery than the second web material, the second web material, once stretched during application to a wearer's body, will remain in the elongated conformation.

Alternatively, the second web dimensions may be increased in the region of the second web opening to increase elasticity in the apertured zones. Preferably, the web thickness is increased in the first opening region at about the second opening in the second material.

Thus, the second web in combination with the base web provides a composite material characterized by good structural integrity and mechanical strength which however is adjustably conformable to body parts, e.g., arms and legs, of significantly varying sizes. The material composite maintains a certain amount of elastic memory and yet yields when the strain on the composite is high and adjusts to a larger sized opening.

In a preferred embodiment, not shown, a ring of third material having an aperture greater than the second opening and outer diameter smaller than the first opening is concentrically aligned within the first opening and overlayed with the second web. The third material may be a heat-shrinkable elastomer. As such it would result following application of heat in a stretchable leg gather, providing fit, protection and comfort and a gathered appearance. This ring would also provide added extensibility and higher elastic recovery than even the second material.

Herein and in the claims, the base web is characterized as a less extensible, lower elastic recovery material in contrast to the second web, which is characterized as a more extensible, higher elastic recovery material. It will therefore be understood that the terms "less extensible," "more extensible," "lower elastic recovery" and "higher elastic recovery" are relative comparative terms having reference to one another, regardless of the absolute values of any specific parameters of physical properties used to measure these characteristics.

As used herein and in the claims, term "extensible" refers to the degree of elongation of the material under consideration when subjected to a tensioning force, so that in pratical terms, the base web, which is the less extensible of the base web and second web components is less stretchable than the second web material. "Elastic recovery" refers to the extent of contraction of the material under consideration when a previously applied tensioning force is released, greater extents of contraction corresponding to higher elastic recovery.

The base web, i.e., the web of less extensible, lower elastic recovery material in the composite of the present invention, may be formed of any suitable film, fibrous or other web material. Illustrative materials of construction for the base web include cast or blown films of polyolefins, such as polyethylene, polypropylene, and copolymers of polyethylene or polypropylene, as well as blends or co-extrusions of such materials. The base web when formed of a fibrous material may be woven or nonwoven in character, and may be formed of any suitable natural and/or synthetic fibers. Illustrative fiber materials include textile fibers such as cotton, rayon, chisso, etc., as well as polyester, polypropylene, polyamides, etc., and compatible blends and mixtures of the foregoing. A preferred material is a firmly bonded polypropylene staple fiber in a nonwoven web, with spun bonded polypropylene being most preferred.

The second web, i.e., the web of more extensible, higher elastic recovery material in the composite of the present invention, may be any suitable film or web of material which may be physically or otherwise joined to the base web material to form a composite comprising same. Preferred second web materials include films of thermoplastic and/or elastomeric composition, with thermoplastic elastic films being most preferred. Illustrative thermoplastic elastic films may be formed of materials such as polypropylene, polyethylene, copolymers of polyethylene (e.g., ethylene methyl acrylate, ethylene vinylacetate, ethylene ethyl acrylate), styrene/butadiene block copolymers, and compatible copolymers, blends and physical mixtures of two or more of the foregoing materials. The second web is preferably in ethylene acrylate film, and more preferably an ethylene methyl acrylate (EMA) film.

The thermoplastic elastic materials mentioned in the preceding paragraph are preferred due to their ability to be extrusion coated in film form onto the base web, or otherwise laminated in sheet form with the base web under conditions of elevated heat and/or pressure.

As used herein, elastic or elastomeric materials are those which are stretchable, i.e., extensible, to an elongation of at least about 25% of their relaxed lengths, i.e., which can be stretched to about one and one-quarter times their relaxed lengths, and upon release of the stretching force will recover at least about 40% of the elongation, i.e., will, in the case of 25% elongation, contract to an elongation of not more than about 15%. For example, a 100 centimeter length of material will, under the foregoing definition, be suitably elastic if it can be stretched to a length of at least about 125 centimeters and if, upon release of the stretching force, it contracts, in the case of being stretched to 125 centimeters, to a length of not more than about 115 centimeters. Of course, numerous elastic materials suitable in the broad practice of the present invention as preferred materials of construction of the second web can be stretched to elongations considerably in excess of 25% of their relaxed length, and many, upon release of the stretching force, will recover to their original relaxed length or very close thereto. At least for some purposes of the present invention, elastic materials which upon release of the stretching force recover all or nearly all of their elongation are most preferred.

Although it is preferred in practice to extrusion coat the second web material in film form onto the base web, or alternatively to laminate the second web to the base web under elevated temperature and/or pressure conditions, i.e., consolidate the respective base and second web layers into a composite under heat and/or pressure, it is within the general purview of the present invention, to utilize other methods of joining the base and second webs to one another, including adhesive bonding, covalent or other chemical bonding, such as by reaction between surface functional groups on the opposed faces of the respective base web and second web, and in any other suitable manner whereby the respective webs may be joined to form a composite therefrom.

Although, as previously indicated, the invention has utility for the fabrication of garments generally, as well as tents, sleeping bags, etc., the invention is particularly advantageously employed in the construction of incontinence control garments, surgical gowns and the like, as well as feminine hygiene and infant care products where adjustable conformable regions are required to maintain fit and prevent leakage.

The first openings provided in the base web, may in practice range in size from an open area of one square millimeter to one square meter, with open areas of from about one square centimeter to 0.5 square meters being preferred for the aforementioned garment applications, however, the size as well as shape of such openings can be any size or dimension needed to achieve proper stretch and fit in the desired end use application. These openings suitably can be rotary die cut prior to joining the base web to the second web, so that the second web may be joined to the base web with a continuous surface over the first openings therein, following which smaller-sized concentric openings (second openings) can be cut, such as by die cutting, in the second web material over the first opening. In such manner, the smaller opening is circumferentially peripherally bounded by an annular-shaped segment of the second web, with such annular-shaped segment in turn being circumferentially peripherally bounded by the base web surrounding the first opening.

Referring now to the drawings, there is shown in FIG. 1 a plan view, in partial section, of a composite web 10 according to one embodiment of the present invention. The composite web comprises base web 11 of less extensible, lower elastic recovery material with a series of spaced-apart first openings 12 therein. The base web is overlaid by a second web 13 of more extensible, higher elastic recovery material having second openings 14 therein. Second openings 14 are generally concentrically arranged with respect to the first openings 12, to form annular segments 15 of the second web material peripherally overlaying the first openings 12, i.e., so that the opening 14 is circumferentially peripherally bounded by the ring-shaped annular segment 15, which in turn is bounded by the material of base web 11 which circumferentially bounds and defines the first openings 12.

Figure 2:
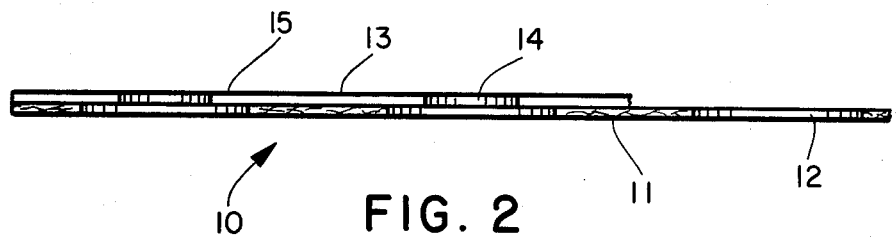
FIG. 2 is a side elevational view of the FIG. 1 web, taken along line 2—2 thereof.

The details of FIG. 1 construction are shown more clearly in FIG. 2, which is a side elevational view of the composite 10, whereby the relationship of the annular segments 15 to the first openings 12 may be more fully appreciated.

Figure 3:
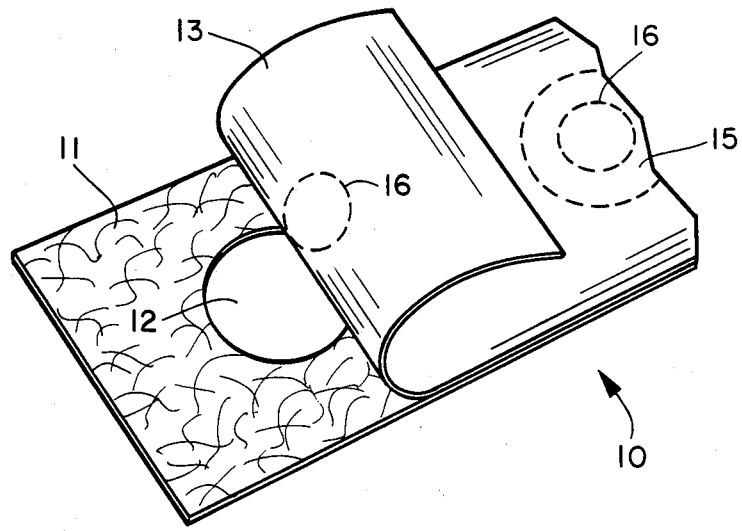
FIG. 3 is a perspective view of a portion of the FIGS. 1-2 composite, wherein the second web is shown during its application to the base web.

The reference numerals in FIG. 2 are numbered correspondingly with respect to the same or analogous elements in FIG. 1, and FIG. 3 likewise is numbered correspondingly with respect to FIGS. 1–2.

FIG. 3 is a perspective view of a portion of the composite 10, showing the application of second web 13 to the base web 11 containing first openings 12. As shown, the second web 13 is in the form of a sheet, e.g., of elastic thermoplastic material, and is laid on the top main surface of base web 11 so as to be lengthwise and widthwise coextensive therewith, and so that the second web presents a continuous film over the first openings 12 in the base web. Shown on the superposed second web overlaying the aperture in the base web is a second opening cut line 16, at which the second web may be die cut or otherwise cut to form the annular segment 15 as illustrated in FIGS. 1 and 2.

Figure 4:
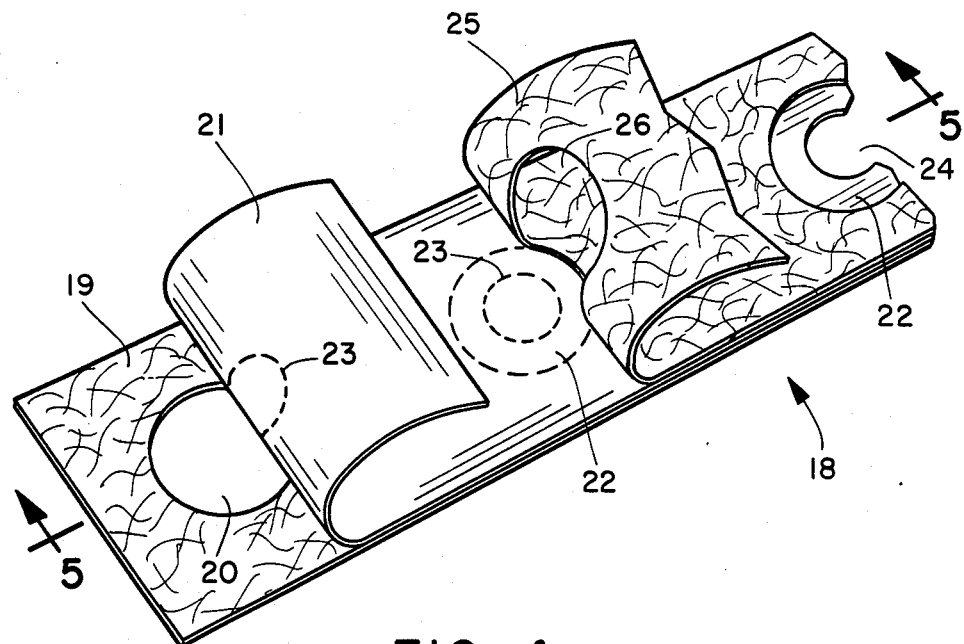
FIG. 4 is a perspective view of a composite according to another embodiment of the present invention showing the application of upper and lower base webs to the second web, to form a tri-layered composite.

FIG. 4 is a perspective view of a composite 18 according to another embodiment of the present invention, wherein the base web 19 is provided with a series of spaced-apart first openings 20 and is coextensively overlaid with a second web 21 of more extensible, higher elastic recovery material, as compared to the base web, to provide a continuous film overlaying the apertures 20 which may be die cut along cut line 23 to form the annular segments 22, analogous to the previously described FIGS. 1–3 embodiment. In this composite, however, another base web, upper base web 25, of less extensible, lower elastic recovery material, as compared to web 21 is provided with first openings 26 of the same size as the first openings 20 in lower base web 19 and positioned to be concentrically superposed therewith. This is more clearly shown in FIG. 5, which is a side elevational view of the FIG. 4 composite 18, wherein the respective edges of first openings 20 and 26 are vertically aligned when the web is disposed on a horizontal surface. In such manner, the intermediate or interposed second web 21 provides the adjustable conformable opening 24 surrounded by annular segment 22 of the second web material, with the annular segment being circumferentially bounded by respective peripheral edges of first openings 20 and 26, respectively.

FIGS. 6–9 show consecutive views in the processing of a composite according to the present invention to form discrete pant-type garments, of a type such as are, for example, usefully employed for training panties for infants and/or toddlers.

Figure 5:
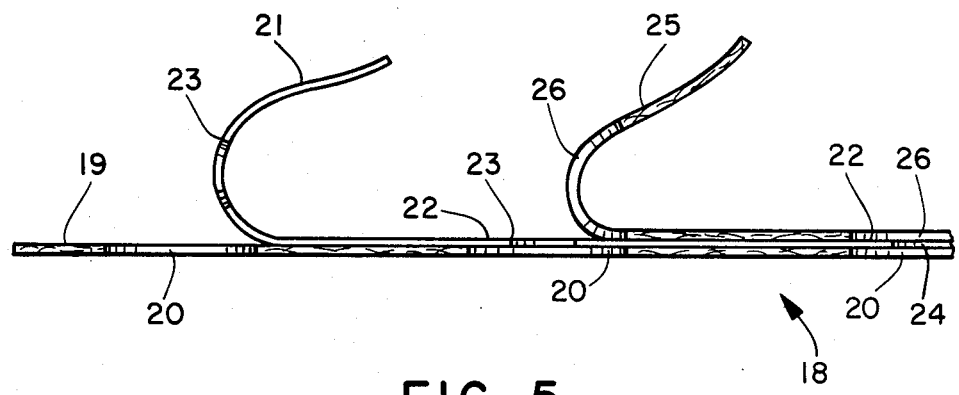
FIG. 5 is a side elevational view of the composite of FIG. 4.

As shown, the composite 30, which may be of two-ply construction of a type shown and described in connection with FIGS. 1–3, of three-ply type as shown and described in connection with FIGS. 4–5, or of other multi-ply construction, has a series of longitudinally spaced-apart, transversely centered adjustable conformable openings 31, 32, 33 and 34, each of which is circumferentially peripherally bounded by the annular segments 35, 36, 37 and 38, respectively, in the previously described manner. Thus the composite 30 is longitudinally extending and is characterized by a longitudinal center line L—L and by longitudinally spaced-apart imaginary transverse lines a—a, b—b and c—c. Each of the adjustable conformable openings 31, 32 and 33 are positioned with their respective centers being intersected by the longitudinal center line and by transverse lines a—a, b—b and c—c, respectively.

Figure 6:
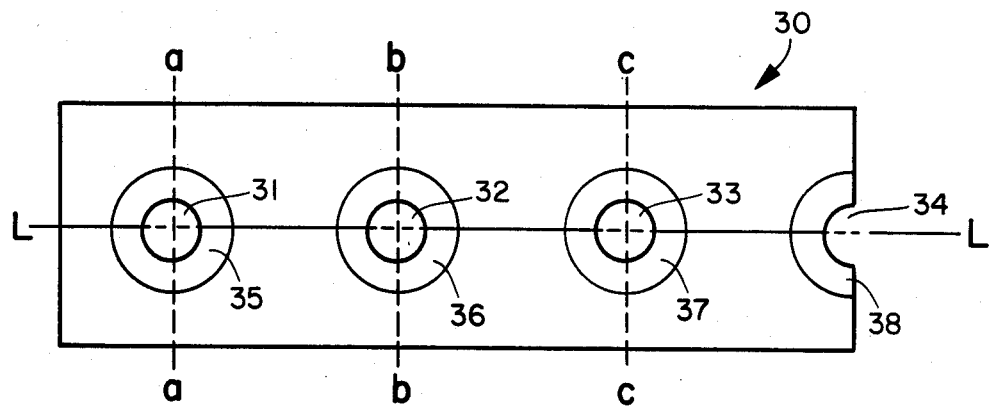
FIG. 6 is a plan view of a composite according to an embodiment of the present invention having a series of longitudinally spaced-apart transversely centered adjustable, conformable openings.
Figure 7:
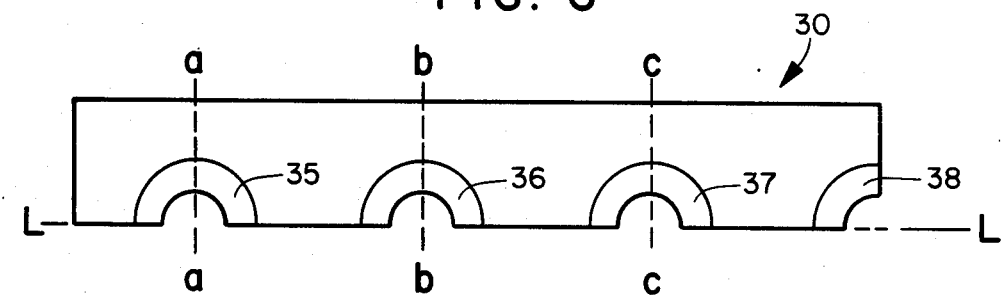
FIG. 7 is a plan view of the web of FIG. 6 as folded along the longitudinal center line L—L.
Figure 8:
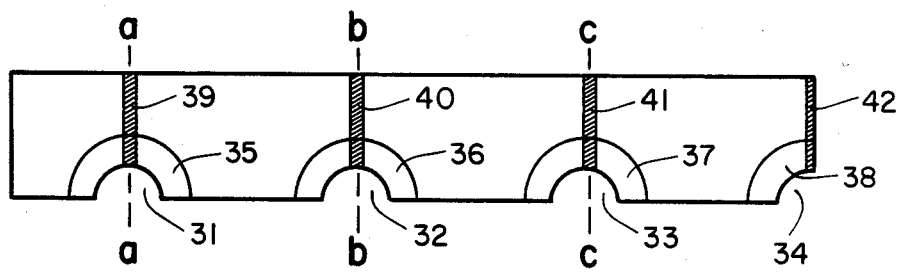
FIG. 8 is a plan view of FIG. 7 composite, on which bonded transverse bands have been formed.

The processing of the web shown in FIG. 6 to form the aforementioned discrete pant-type garments therefrom involves folding of the web along the longitudinal center line L—L, to provide the configuration shown in FIG. 7, wherein all parts and elements are numbered correspondingly with respect to the same elements in FIG. 6. Next, as shown in FIG. 8, the longitudinally folded composite is bonded over the areas indicated by transverse bands 39, 40, 41 and 42. The bonding of the transverse band areas may be carried out by any suitable means, such as by ultrasonic fusion welding, thermal pattern roll embossing, etc. The respective bonded transverse bands 39, 40 and 41 are positioned so that there is a generally equivalent amount of bonded area of either side of the transverse lines a—a, b—b and c—c.

Figure 9:
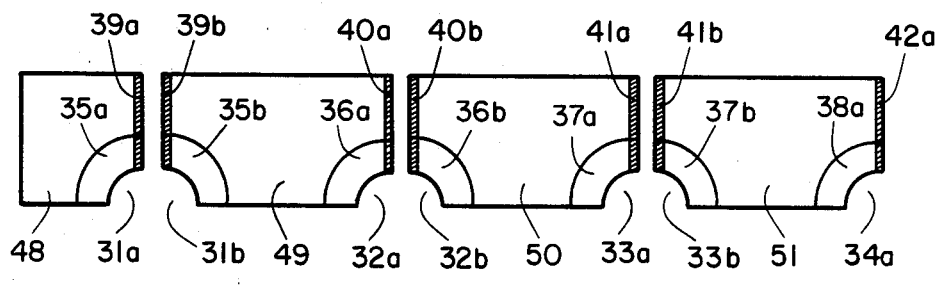
FIG. 9 shows a series of discrete severed articles formed by medially severing the bonded transverse bands of the FIG. 8 composite.

Finally, the longitudinally folded, transversely bonded composite shown in FIG. 8 is medially severed at the transverse bands 39, 40 and 41 by cutting the composite along lines a—a, b—b and c—c, respectively to form the discrete severed articles 48, 49, 50 and 51, as shown in FIG. 9.

The respective severed articles are bounded by side seams derived from the corresponding transverse bands, the severing of transverse band 39 providing side seams 39a and 39b, the severing of transverse band 40 providing side seams 40a and 40b, the severing of transverse band 41 providing side seams 41a and 41b, and the severing of the transverse band 42 providing side seam 42a.

In like manner, the severing of the annular segments 35, 36, 37 and 38 provide corresponding arcuate segments 35a, 35b; 36a, 36b; 37a, 37b; and 38a, respectively. These arcuate segments of the second web, by virtue of the respective side seams, completely enclose the adjustable conformable openings 31a, 31b; 32a, 32b; 33a, 33b; and 34a derived from the corresponding second openings, 31, 32, 33 and 34, respectively.

The discrete severed articles thus form pant-type garments which are conformably adjustable to various sized legs of wearers, and concomitantly provide an adjustable, conformable fit to the individual wearer's leg to insure leak tightness.

Although not specifically disclosed, it will be apparent that the waist areas of the pant-type garments may be provided with suitable elastic or other gathering means to provide a conformable fit, or alternatively, the composite construction of the present invention may also be used in the waist area to provide a conformable fit thereat.

Further, although not specifically described, it will be appreciated that the pant-type garments may have interiorly disposed therein absorbent pad units or other body exudate sorption means, as conventionally employed in the art.

The advantages of features of the present invention will be more fully apparent with reference to the ensuing example.

EXAMPLE

A composite according to one embodiment of the present invention is formed from a base web of spun bonded polypropylene fibers and to this nonwoven substrate is applied by extrusion coating or lamination a thermoplastic film of ethylene methyl acrylate (EMA) at a temperature of 275° C. to 315° C., preferably at a temperature of at least 293° C. and a film thickness of about 0.4 to 10 mils, and more preferably from about 0.4 to 2 mils thickness. In the case of extrusion coating, the aforementioned temperature is the temperature measured at the extruder screw, and the extruded film is brought into pressure contact with the base web comprising the nonwoven polypropylene spun bonded web and pressed together so that the thermoplastic film and the base web yield a resulting composite suitable for the manufacture of pant-type garments as described herein with reference to FIG. 6–9 hereof.

Although preferred embodiments of the present invention have been described in detail, it will be appreciated that other modifications and variations of the disclosed embodiments, together with other embodiments, are possible, and accordingly all apparent modifications, variants and embodiments are to be regarded as being within the spirit and scope of the present invention.

What is claimed is:

1. A composite with an adjustable, conformable opening therein, comprising a base web of less extensible, lower elastic recovery material joined to a second web, of more extensible, higher elastic recovery material, wherein said base web has a first opening therein, and said second web has a second opening therein generally concentric with the first opening and of smaller size than said first opening, so that the second opening is circumferentially peripherally bounded by an annular-shaped segment of said second web, and said annular-shaped segment of said second web in turn is circumferentially peripherally bounded by said base web.

2. A garment comprising the composite web of claim 1, wherein said second opening is a conformable body part opening.

3. A composite according to claim 1, wherein the second web has a base web joined to each of its respective sides.

4. A composite according to claim 1, wherein the base web comprises a fibrous material.

5. A composite according to claim 4, wherein said fibrous material is woven.

6. A composite according to claim 4, wherein said fibrous material is nonwoven.

7. A composite according to claim 1, wherein the second web is a thermoplastic material.

8. A composite according to claim 1, wherein the second web is an elastomeric material.

9. A composite according to claim 1, wherein the second web is joined to the base web by lamination therewith.

10. A composite according to claim 1, wherein the second web is joined to the base web by melt extrusion of the second web onto the base web.

11. A composite according to claim 1, wherein the thickness of the second web contiguous the second opening is greater than the thickness of the web outside the region of the first opening.

12. A composite according to claim 1, wherein said first opening is fitted with a third web having a third opening generally concentric with said second opening and of an equal or greater size than said second openings, said second web being joined to said third web.

13. A pant garment with conformable leg openings, formed of superposed front and back panels joined to one another along side and central bottom portions with the respective side and central bottom portions separated from each other by unjoined arcuately contoured portions of the front and rear panels to form leg openings for the garment, wherein the front and rear panels of the garment at least in the vicinity of said leg openings are formed of a composite comprising a base web of less extensible, lower elastic recovery material joined to a second web of more extensible, higher elastic recovery material, wherein the leg openings are circumferentially bounded by annular arcuate segments of only said second web, extending from said composite comprising said base web and second web.

* * * * *